United States Patent

Shiokawa et al.

Patent Number: 5,719,146
Date of Patent: Feb. 17, 1998

[54] INSECTICIDAL HETEROCYCLIC COMPOUNDS

[75] Inventors: Kozo Shiokawa, Kanagawa-ken; Shinichi Tsuboi, Tokyo; Koichi Moriya, Tokyo; Yumi Hattori, Tokyo; Ikuro Honda, Tokyo; Katsuhiko Shibuya, Tokyo, all of Japan

[73] Assignee: Nihon Bayer Agrochem K.K., Tokyo, Japan

[21] Appl. No.: 597,780

[22] Filed: Feb. 7, 1996

Related U.S. Application Data

[62] Division of Ser. No. 870,178, Apr. 16, 1992, which is a continuation of Ser. No. 658,933, Feb. 21, 1991, abandoned, which is a continuation of Ser. No. 487,004, Mar. 1, 1990, Pat. No. 5,032,589.

[30] Foreign Application Priority Data

Mar. 9, 1989  [JP]  Japan ......................... 1-54943

[51] Int. Cl.$^6$ ............................ A01N 43/88; C07D 413/06
[52] U.S. Cl. ............................ 514/229.2; 544/67
[58] Field of Search .................... 544/67; 514/229.2

[56] References Cited

U.S. PATENT DOCUMENTS 2,654,741  10/1953  Rhodehamel, Jr. .
4,803,277  2/1989  Shiokawa et al. .

FOREIGN PATENT DOCUMENTS 0580553  1/1994  European Pat. Off. .

OTHER PUBLICATIONS

Seidel et al., *J. Het. Chem.*, 9: 231 (1972).
Takimoto et al., *Bull.Chem.Soc.Jpn.*, 56: 3319 (1983).

Hawley's Condensed Chemical Dictionary, 11th Edition, Sax et al., Editors, Van Nostrand Reinhold, NY, 1987, pp. 333, 383, 536–7 and 830.

*Primary Examiner*—Patricia L. Morris
*Attorney, Agent, or Firm*—Sprung Kramer Schaeffer & Briscoe

[57] ABSTRACT

Insecticidal heterocyclic compounds of the formula

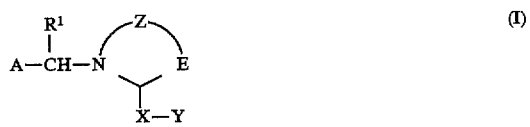

wherein A represents a five-membered or six-membered heteroaryl group containing one to three hetero atoms selected from the group consisting of S, O and N, said heteroaryl group being unsubstituted or substituted by a halogen atom or $C_{1-4}$ alkyl group, Z represents a three-membered straight chain, each member being selected from the group consisting of $CH_2$—, O, S and N—$R^2$ with at least one of said three members being O, S or N—$R^2$, E represents $CH_2$, O, S or N—$R^2$, wherein $R^2$ represents a hydrogen atom, a $C_{1-4}$ alkyl group, a $C_{1-4}$ alkoxy group or the group

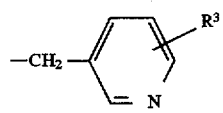

wherein $R^3$ represents a hydrogen atom or halogen atom, X represents CH or N, Y represents a nitro group or cyano group, and $R^1$ represents a hydrogen atom or methyl group.

3 Claims, No Drawings

INSECTICIDAL HETEROCYCLIC COMPOUNDS

This application is a divisional of application Ser. No. 07/870,178, filed Apr. 16, 1992, now pending; which is a continuation of Ser. No. 07/658,933, abandoned; which is a continuation of Ser. No. 07/487,004, filed Mar. 1, 1990, issued to U.S. Pat. No. 5,032,589.

The present invention relates to novel heterocyclic compounds, to a process for their preparation, and to their use as insecticides.

It has already been disclosed that 2-(nitromethylene) oxazolines have insecticidal activities (see ADVANCES IN PESTICIDE SCIENCE Part 2, pages 206 to 217. That article relates to symposia papers presented at the Fourth International Congress of Pesticide Chemistry, Zurich, Switzerland, Jul. 24–28, 1978, published by Pergamon Press).

There have been found novel heterocyclic compounds of the formula (I),

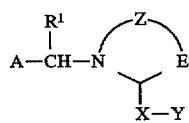
(I)

wherein A represents a five-membered or six-membered heteroaryl group comprising one to three hereto atoms selected from the group consisting of S, O and N, said heteroaryl group being unsubstituted or substituted by a halogen atom or $C_{1-4}$ alkyl group, Z represents a three-membered straight chain each member being selected from the group consisting of $CH_2$, O, S and N—$R^2$ with at least one of said three members being O, S or N—$R^2$, E represents $CH_2$, O, S or N—$R^2$, wherein $R^2$ represents a hydrogen atom, a $C_{1-4}$ alkyl group, a $C_{1-4}$ alkoxy group or the group

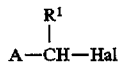

wherein $R^3$ represents a or the group hydrogen atom or halogen atom, X represents CH or N, Y represents a nitro group or cyano group, and $R^1$ represents a hydrogen atom or methyl group.

Novel heterocyclic compounds of the formula (I) are obtained when the compounds of the following formula (II)

$$R^1$$
$$|$$
$$A—CH—Hal$$
(II)

wherein A and $R^1$ have the same meanings as mentioned above, and Hal means a halogen atom, are reacted with the compounds of the following formula (III)

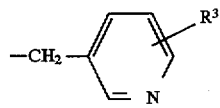
(III)

wherein Z, E, X and Y have the same meanings as mentioned above, if appropriate in the presence of an acid binder, and in the presence of inert solvents.

The novel heterocyclic compounds of the formula (I) exhibit powerful insecticidal properties.

Surprisingly, the heterocyclic compounds according the invention exhibit a substantially greater insecticidal action than those known from the prior art, for instance, than those of the above-mentioned article "ADVANCES IN PESTICIDE SCIENCE Part 2".

Among the heterocyclic compounds according to the invention, of the formula (I), preferred compounds are those in which A represents 2-chloropyridin-5-yl or 2-chlorothiazol-5-yl, Z represents a three-membered straight chain, each member being selected from the group consisting of $CH_2$, O, S and N—$R^2$ with at least one of said three members being O, S or N—$R^2$, E represents $CH_2$, O, S or N—$R^2$, wherein $R^2$ represents a $C_{1-3}$ alkyl group, a $C_{1-3}$ alkoxy group or 2-chloropyridin-5yl methyl, X represents N, and Y represents a nitro group or cyano group.

If, for example, 2-chloro-5-chloromethylpyridine and 3-cyanoiminomorpholine are used as starting materials, the course of the reaction can be represented by the following equation:

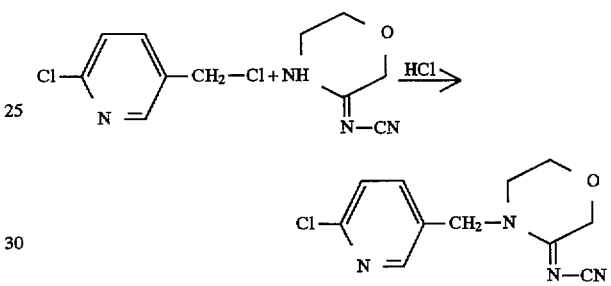

In the compound of the formula (II), A, $R^1$ and Hal have the same meanings as defined above, preferably A and $R^1$ have the same meanings as the above preferred meanings. Hal preferably stands for a chlorine atom.

The compounds of the formula (II) to be used according to the invention are already known. As examples there may be mentioned the following:

5-chloromethyl-2-chlorothiazole, 2-chloro-5-chloromethyl-pyridine, 5-chloromethyl-2-methylthiazole, 5-chloromethyl-2-fluoropyridine, 5-chloromethyl-3-methyl-isoxazole, 2-bromo-5-chloromethyl pyridine, and 5-chloromethyl-2-methylpyridine.

In the compound of the formula (III), Z, E, X and Y have the same meanings as defined above, preferably Z, E, X and Y have the same meanings as the above preferred meanings.

Some of the starting materials of the formula (III) are novel, and can be obtained as outlined below. For example, 3-cyano-iminomorpholine can be obtained when compounds of the formula (IV)

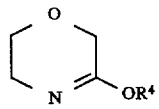
(IV)

wherein $R^4$ represents a lower alkyl group are reacted with cyanamide in the presence of an inert solvent.

The compounds of the formula (IV) are novel and can be obtained when 3-morpholinone of the following formula

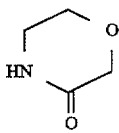

is reacted with compounds of the following formula (V)

$$(R^4O)_2SO_2 \quad (V)$$

wherein $R^4$ has the same meaning as mentioned above, in the presence of an inert solvent. 3-Morpholinone is already known from Chemical Abstracts, Vol.47, 2761e. and the compounds of the formula (V) are also known compounds in the field of organic chemistry.

3-Nitroiminomorpholine of the formula (III) can be obtained when 3-amino-2H-1,4-dihydrooxazine of the following formula (VI)

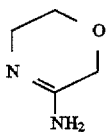

is reacted with fuming nitric acid, in the presence of an inert solvent.

The compound of formula (VI) is novel and can be obtained, for example, when the compounds of the formula (IV) are reacted with ammonia.

3-nitromethylene morpholinone of the above-mentioned formula (III) can be obtained when compounds of the formula (IV) are reacted with nitromethane, in the presence of inert solvents.

In the case where the compounds of formula (III) are represented by the following general formula (III'):

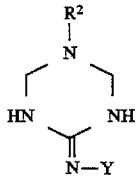

wherein $R^2$ and Y have the same meanings as mentioned above, those compounds of formula (III') can be obtained when compounds of the formula (VII)

$$R^2-NH_2 \quad (VII)$$

wherein $R^2$ has the same meaning as mentioned above, are reacted with nitroguanidine or cyanoguanidine in the presence of formaldehyde.

In carrying out process (a) mentioned above, any inert solvent can be used as diluent.

Examples of such diluents are water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, 1,2-dichloroethane, chlorobenzene, dichlorobenzene and the like; ethers such as diethyl ether, methyl ethyl ether, di-isopropyl ether, dibutyl ether, propylene oxide, dioxane, tetrahydrofuran and the like; ketones such as acetone, methyl ethyl ketone, methyl isopropyl ketone, methyl isobutyl ketone and the like; nitriles such as acetonitrile, propionitrile, acrylonitrile and the like; alcohols such as methanol, ethanol, iso-propanol, butanol, ethylene glycol and the like; esters such as ethyl acetate, amyl acetate and the like; acid amides such as dimethyl formamide, dimethyl acetamide and the like; and sulfones and sulfoxides such as dimethyl sulfoxide, sulfolane and the like; and bases, for example, pyridine, etc.

The above-mentioned process (a) may be carried out in the presence of an acid binder such as, for example, a hydroxide, carbonate, bicarbonate, alcoholate of an alkali metal, and tertiary amines such as, for example, triethylamine, diethyl aniline, pyridine, etc.

In the process (a), the reaction temperature can be varied within a wide range. In general, the reaction is carried out at a temperature of about 0° to 100° C., preferably at about 30°–80° C. In general, the reaction is allowed to proceed under normal pressure, although it is also possible to employ a higher or lower pressure.

When the process (a) according to the invention is carried out, use is made, for instance, of about 1 to 1.1 moles of the compounds of the general formula (II) per mole of the compounds of the general formula (III) in the presence of an inert solvent such as acetonitril and 1.0 to 1.2 moles of potassium carbonate to obtain the desired compounds.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example Oniscus Asellus, *Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp.,

*Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp.,Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia pp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the individual use forms.

When used against hygiene pests and pests of stored products, the active compounds are distinguished by an excellent residual action on wood and clay as well as a good stability to alkali on limed substrates.

The preparation and use of the active compounds according to the invention can be seen from the following examples.

Examples of Preparation
Example 1

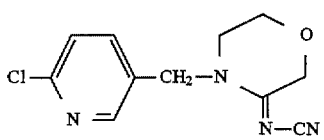

3-Morpholinone(10.1 g) was dissolved in toluene (100 ml) and the solution was heated to 70° C. To the resulting solution dimethyl sulphate (12.6 g) was added dropwise over a period of 30 minutes. After the completion of this addition, the reaction mixture was heated under reflux for 6 hours. After having been allowed to cool, the reaction mixture was admixed portionwise with anhydrous potassium carbonate (13.8 g), while being kept in an ice bath.

After one hour stirring, the separated salt was filtered off and the filtrate was concentrated to obtain crude 3-methoxy-5,6-dihydro-2H-oxazine (8 g). The thus obtained crude product was dissolved in anhydrous tetrahydrofuran with the addition of cyanamide (2.9 g) thereto, refluxing for three hours under heating. Under reduced pressure, the tetrahydrofuran was distilled off from the solution and the residue was recrystallized from chloroform to obtain 2 g of 3-cyanoiminomorpholine having a melting point of from 169° to 170° C.

The thus obtained 3-cyanoiminomorpholine (1.25 g) was dissolved in acetonitrile (50 ml) with the addition of 2-chloro-5-chloromethylpyridine (1.62 g) and anhydrous potassium carbonate (1.4 g) thereto, followed by a five hour heating under reflux.

After having been allowed to cool, the reaction liquid was poured into iced water and then subjected to extraction with dichloromethane.

The organic layer formed was purified by silica gel column chromatography (eluant: chloroform: ethanol=95: 5) to obtain the desired 4-(2-chloro-5-pyridylmethyl)-3-cyanoiminomorpholine (0.9 g) having a melting point in the range of from 97° to 98.5° C.

Example 2

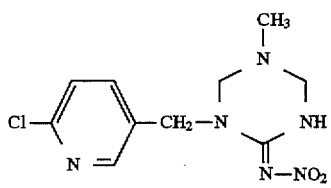

5-Methyl-2-nitroimino-hexahydro-1,3,5-triazine (3.0 g) was dissolved in dimethylformamide/DMF (20 ml), followed by portionwise addition of sodium hydride (950 mg: oil free) thereto at a temperature in the range of from 0° to 5° C. After one hour stirring at 0° to 5° C. a solution of 2-chloro-5-chloromethyl-pyrimidine (3.1 g) in 20 ml of DMF was added dropwise to the solution, the temperature was kept constant, followed by a five hour stirring. The reaction mixture thus obtained was poured into iced water, subjected to extraction with methylene chloride a few times and then the extract was dried with anhydrous magnesium sulfate which was removed from the solvent. The thus obtained residue was purified by silica gel column chromatography (eluant: ethanol: chloroform=1: 20), to obtain the desired 1-(2-chloro-5-pyridylmethyl)-5-methyl-2-nitroimino-hexahydro-1,3,5-triazine (3.7 g) having a melting point in the range of from 160° to 161° C.

Example 3

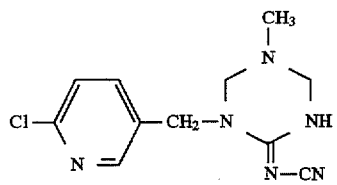

A mixture consisting of 5-methyl-2-cyanoimino-hexahydro-1,3,5-triazine (6.0 g), 5-chloro-2-chloromethylpyridine (7.0 g), anhydrous potassium carbonate (6.6 g) and acetonitrile (80 ml) was heated under reflux for a period of 10 hours. After having been allowed to cool, the separated solid substance was filtered off from the mixture and the filtrate was concentrated under reduced pressure, followed by purification of the resulting residue by column chromatography (eluant: ethanol: chloroform=1: 20) to obtain the desired 1-(2-chloro-5-pyridylmethyl)-5-methyl-2-cyanoimino-hexahydro-1,3,5-triazine (7.5 g) having a melting point in the range of from 198° to 202° C.

Example 4

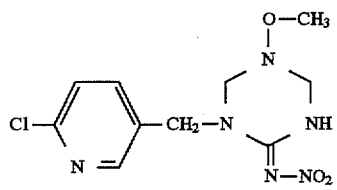

The hydrochloride (10 g) of 5-methoxy-2-nitroimino-hexahydro-1,3,5-triazine was suspended in dimethyl formamide/DMF (180 ml) followed by portionwise addition of sodium hydride (3.4 g oil free) thereto at 0° to 5° C.

After a one hour stirring at a temperature of from 0° to 5° C. a solution of 2-chloro-5-chloromethyl-pyridine (7.7 g) in DMF (20 ml) was added dropwise to the suspension while the above-mentioned temperature was kept constant, followed by a five hour stirring thereof.

The reaction mixture thus obtained was poured into iced water, subjected to extraction with methylene chloride a few times and then the extract was dried with anhydrous magnesium sulfate which was removed from the solvent. The thus obtained residue was purified by silica gel column chromatography (eluant: ethanol: chloroform=1: 20), to obtain the desired 1-(2-chloro-5-pyridylmethyl)-5-methoxy-2-nitroimino-hexahydro-1,3,5-triazine (8.5 g) having a melting point in the range of from 159° to 163° C.

Compounds which can be prepared by processes in analogous to the foregoing examples are shown, together with the compounds obtained in the foregoing Examples 1–4 in the following Table 1.

TABLE 1

| Compound No. | Structure | Physical constant |
|---|---|---|
| 1 | pyridin-4-yl-CH₂-N(morpholinyl-C=N-CN) | |
| 2 | 6-chloropyridin-3-yl-CH₂-N(morpholinyl-C=N-CN) | mp. (°C.) 97–98.5 |
| 3 | 2-chlorothiazol-5-yl-CH₂-N(morpholinyl-C=N-CN) | mp. (°C.) 158–159 |
| 4 | 6-methylpyrazin-3-yl-CH₂-N(morpholinyl-C=N-CN) | |
| 5 | 4-bromoisoxazol-5-yl-CH₂-N(morpholinyl-C=N-CN) | |
| 6 | 6-chloropyridin-3-yl-CH₂-N(morpholinyl-C=N-NO₂) | |
| 7 | 2-chlorothiazol-5-yl-CH₂-N(morpholinyl-C=N-NO₂) | |
| 8 | 6-chloropyridin-3-yl-CH₂-N(morpholinyl-C=CH-NO₂) | |
| 9 | 2-chlorothiazol-5-yl-CH₂-N(morpholinyl-C=CH-NO₂) | |
| 10 | furan-3-yl-CH₂-N(N-methyl-hexahydrotriazinyl-C=N-NO₂) | |

TABLE 1-continued

| Compound No. | Structure | Physical constant |
|---|---|---|
| 11 | 6-chloropyridin-3-yl-CH₂ group attached to triazinane with N-CH₃ and =N-NO₂ | mp. (°C.) 160–161 |
| 12 | 2-chlorothiazol-5-yl-CH₂ group attached to triazinane with N-CH₃ and =N-NO₂ | mp. (°C.) 157–161 |
| 13 | 3-isobutyl-1,2,4-oxadiazol-5-yl-CH₂ group attached to triazinane with N-CH₃ and =N-NO₂ | |
| 14 | 6-chloropyridin-3-yl-CH₂ group attached to triazinane with N-OCH₃ and =N-NO₂ | mp. (°C.) 159–163 |
| 15 | 6-chloropyridin-3-yl-CH₂ group attached to triazinane with N-CH(CH₃)₂ and =N-NO₂ | $n_D^{20}$ 1.5812 |
| 16 | bis(6-chloropyridin-3-yl-CH₂) groups attached to triazinane with N-CH(CH₃)₂ and =N-NO₂ | mp. (°C.) 66–70 |
| 17 | 6-chloropyridin-3-yl-CH₂ group attached to triazinane with N-CH₃ and =N-CN | mp. (°C.) 198–202 |
| 18 | 1,2,5-thiadiazol-3-yl-CH₂ group attached to triazinane with N-CH₃ and =N-CN | |

TABLE 1-continued

| Compound No. | | Physical constant |
|---|---|---|
| 19 | 2-chloro-thiazol-5-yl-CH₂-N attached to a 6-membered ring containing N-CH₃, with =N-CN and NH substituents | |
| 20 | 2-methyl-thiazol-5-yl-CH₂-N attached to a 6-membered ring containing N-CH₃, with =N-CN and NH substituents | |
| 21 | 5-chloro-thiophen-3-yl-CH₂-N attached to a 6-membered ring containing N-CH₂CH₃, with =N-CN and NH substituents | |
| 22 | 2-methyl-pyrimidin-5-yl-CH₂-N attached to a 6-membered ring containing N-CH₂CH₂CH₃, with =N-CN and NH substituents | |
| 23 | 6-chloro-pyridin-3-yl-CH₂-N attached to a 6-membered ring containing S, with =N-NO₂ and NH substituents | |
| 24 | 3-methyl-isoxazol-5-yl-CH₂-N attached to a 6-membered ring containing O, with =CH-NO₂ | |
| 25 | 6-methyl-pyridin-3-yl-CH₂-N attached to a 6-membered ring containing O, with =N-NO₂ | |
| 26 | 6-chloro-pyridin-3-yl-CH₂-N attached to a 6-membered ring containing O, with =CH-NO₂ | |
| 27 | 1-methyl-pyrazol-4-yl-CH₂-N attached to a 6-membered ring containing O and S, with =CH-NO₂ | |

TABLE 1-continued

| Compound No. | | Physical constant |
|---|---|---|
| 28 | [structure: 6-chloropyridin-3-yl-CH2-N in ring with O-CH2-CH2-S, =CH-NO2] | |
| 29 | [structure: 6-chloropyridin-3-yl-CH2-N in ring with O-CH2-CH2-S, =N-NO2] | |
| 30 | [structure: 6-methylpyrazin-2-yl-CH2-N in ring with NH-NH-CH2-CH2, =N-CN] | |
| 31 | [structure: 6-chloropyridin-3-yl-CH2-N in ring with NH-NH-CH2-CH2, =CH-NO2] | |
| 32 | [structure: 6-chloropyridin-3-yl-CH2-N in ring with NH-NH-CH2-CH2, =N-NO2] | |
| 33 | [structure: 2-methylthiazol-5-yl-CH2-N in ring with NH-NH-CH2-CH2, =CH-NO2] | |
| 34 | [structure: pyridin-3-yl-CH2-N in ring with O-CH2-CH2-NH, =N-NO2] | |
| 35 | [structure: 6-chloropyridin-3-yl-CH2-N in ring with O-CH2-CH2-NH, =CH-NO2] | |
| 36 | [structure: 2-methylthiazol-5-yl-CH2-N in ring with O-CH2-CH2-NH, =N-NO2] | |
| 37 | [structure: 6-chloropyridin-3-yl-CH2-N in ring with NH-O-CH2-CH2, =N-CN] | |

TABLE 1-continued

| Compound No. | | Physical constant |
|---|---|---|
| 38 | Cl—[pyridine]—CH$_2$—N(CH$_2$CH$_2$O)—C(=CH—NO$_2$)—NH | |
| 39 | Cl—[pyridine]—CH$_2$—N(CH$_2$CH$_2$O)—C(=N—NO$_2$)—NH | |
| 40 | (CH$_3$)$_2$CH—C(=N—O)—N=C(CH$_3$)—CH$_2$—N[piperazine-N(CH$_3$)]—C(=N—NO$_2$)—NH | mp. (°C.) 106–110 |

Example 5 (Preparation of an intermediate compound)

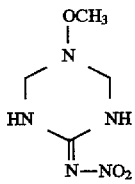

A mixture consisting of nitroguanidine (10 g), methoxyamine hydrochloride (9.6 g), 75% paraformaldehyde (11.5 g), toluene (80 ml) and a catalytic amount of concentrated hydrochloric acid was subjected to heating under reflux for three hours, while the water was removed therefrom. Under reduced pressure, the solvent contained in the mixture was distilled off to obtain white crystals of the hydrochloride of 5-methoxy-2-nitroimino-hexahydro-1,3,5-triazine (16.2 g) having a melting point from 160° to 170° C.

Example 6

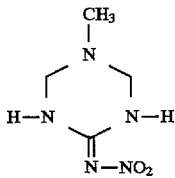

A mixture of nitroguanidine (21 g), 40% aqueous solution of methyl amine (15.7 g) and formalin (40 ml) was stirred at a temperature of from 50° to 60° C. for one hour, followed by distillation thereof under reduced pressure, thus removing the solvent therefrom to obtain a residue that was in turn recrystallized from ethanol, to form 5-methyl-2-nitroimino-hexahydro-1,3,5-triazine (2.6 g) having a melting point in the range of from 206° to 210° C. (decomposition).

Example 7

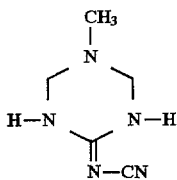

A mixture of cyanoguanidine (21 g), 40% aqueous solution of methyl amine (19.4 g) and formalin (40 ml) was stirred at a temperature from 50° to 60° C. for one hour, followed by distillation thereof under reduced pressure, thus removing the solvent therefrom to obtain a residue that was in turn recrystallized from ethanol, to form 5-methyl-2-cyanoimino-hexahydro-1,3,5-triazine (24 g) having a melting point from 170° to 173° C.

Biotest Examples

Example 8

Biotest carried out against Nephotettix cincticeps (green rice leafhopper) exhibiting resistance to organophosphorus series insecticides Preparation of test formulation Solvent: 3 parts by weight of xylene Emulsifier: 1 part by weight of polyoxyethylene-alkylphenyl-ether To prepare a suitable formulation of an active compound, 1 part by weight of the active compound was mixed with the above amount of the solvent containing the above amount of the emulsifier, and the mixture was diluted with water to the predetermined concentration.

Test Method

Rice plant seedlings about 10 cm high, which were planted in pots of 12 cm diameter were used for the test.

Onto each potted rice-plant seedling, 10 ml aqueous solution of the active compound was sprayed.

After the sprayed solution was dried up, each pot was covered with a cylindrical cage of 7 cm diameter and 14 cm height. Female adults of Nephotettix cincticeps exhibiting resistance to organophosphorus-series insecticides were released into each cage and it was placed in a constant temperature chamber. Two days later the number of insects dead was counted and mortality was calculated.

The active compounds 2, 3, 11, 12, 14, 15, 16, 17 and 40 each exhibited a 100% insect mortality at a concentration of 200 ppm of the active compound, Example 9

Biotest carried out against Myzus persicae exhibiting resistance to organophosphorus and carbamate-series insecticides Test Method Eggplant seedlings (black long eggplant) having a height of 20 cm and planted in unglazed pots (diameter: 15 cm) were used for the test. Onto each seedling, about 200 Myzus persicae adults having resistance against organophosphorus and carbamate-series insecticides were inoculated. One day after the inoculation, an aqueous solution of the active compound, which had been prepared according to the procedure in analogy to Example 8, was sprayed onto the seedlings with a sufficient dosage by a spray gun.

The above-mentioned test was carried out in two replications for each of the below-indicated active compounds with the indicated concentration dosages. The treated seedlings were kept for 24 hours in a greenhouse at 28° C., the number of dead insects was counted and the mortality in % was calculated.

The compounds 2, 3, 11, 12, 14, 15, 16, 17, and 40 each exhibited a 100% insect mortality at a concentration of 500 ppm of the active compound.

It is understood that the specification and examples are illustrative but not limitative of the present invention and that other embodiments within the spirit and scope of the invention will suggest themselves to those skilled in the art.

What is claimed is:

1. A heterocyclic compound of the formula:

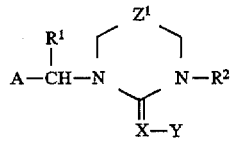

wherein

A represents 2-chloropyridin-5-yl or 2-chlorothiazol-5-yl;

$Z^1$ represents O;

$R^2$ represents a hydrogen atom, a $C_{1-4}$-alkyl group or 2-chloropyridin-5-ylmethyl;

X represents CH or N;

Y represents $NO_2$ or CN; and $R^1$ represents a hydrogen atom or a methyl group.

2. An insecticidal composition comprising an insecticidally effective amount of a compound according to claim 1 and a diluent.

3. A method of combating insects which comprises applying to such insects or to an insect habitat an insecticidally effective amount of a compound according to claim 1.

* * * * *

UNITED STATES PATENT AND TRADEMARK OFFICE
CERTIFICATE OF CORRECTION

PATENT NO : 5,719,146
DATED : February 17, 1998
INVENTOR(S): Shiokawa, et al.

It is certified that error appears in the above-identified patent and that said Letters Patent are hereby corrected as shown below:

Title Page        ABSTRACT: Line 2 delete " 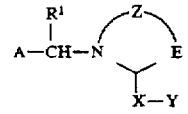 " and substitute -- 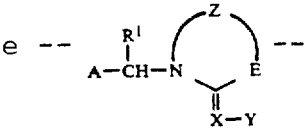 --

Col. 1, line 23    Delete " 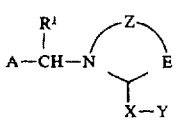 " and substitute

-- 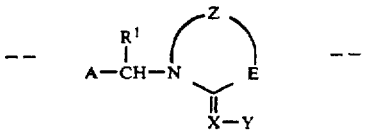 --

UNITED STATES PATENT AND TRADEMARK OFFICE
CERTIFICATE OF CORRECTION

PATENT NO : 5,719,146
DATED : February 17, 1998
INVENTOR(S): Shiokawa, et al.

It is certified that error appears in the above-identified patent and that said Letters Patent are hereby corrected as shown below:

Col. 1, line 58    Delete " 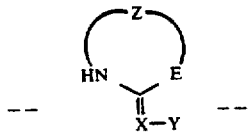 " and substitute

-- 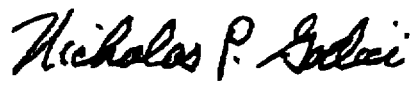 --

Signed and Sealed this

Fifteenth Day of May, 2001

Attest:

NICHOLAS P. GODICI

Attesting Officer    Acting Director of the United States Patent and Trademark Office

Adverse Decisions In Interference

Patent No. 5,719,146, Kozo Shiokawa, Shinichi Tsuboi, Koichi Moriya, Yumi Hattori, Ikuro Honda, Katsuhiko Shibuya, INSECTICIDAL HETEROCYCLIC COMPOUNDS, Interference No. 104,525, final judgment adverse to the patentees rendered June 27, 2001, as to claims 1-3.

*(Official Gazette July 31, 2001)*